United States Patent [19]
Roberts et al.

[11] Patent Number: 5,877,112
[45] Date of Patent: Mar. 2, 1999

[54] AGRICULTURAL FORMULATION

[75] Inventors: Johnnie R. Roberts, Memphis; Greg Volgas, Bartlett, both of Tenn.

[73] Assignee: Helena Chemical Company, Memphis, Tenn.

[21] Appl. No.: 921,200

[22] Filed: Aug. 27, 1997

[51] Int. Cl.⁶ .......................... A01N 25/30; A01N 25/02
[52] U.S. Cl. ...................... 504/116; 71/DIG. 1; 516/57; 516/908
[58] Field of Search ................ 71/DIG. 1; 504/116; 424/405; 252/357

[56] References Cited

U.S. PATENT DOCUMENTS

| | | | |
|---|---|---|---|
| 4,080,191 | 3/1978 | Harvey | 71/DIG. 1 |
| 4,313,847 | 2/1982 | Chasin et al. | 71/DIG. 1 |
| 4,332,609 | 6/1982 | Ott et al. | 71/27 |
| 4,440,562 | 4/1984 | Prill et al. | 71/86 |
| 4,770,694 | 9/1988 | Iwaski et al. | 71/93 |
| 5,178,795 | 1/1993 | Roberts | 252/356 |
| 5,334,585 | 8/1994 | Derian et al. | 71/DIG. 1 |
| 5,389,598 | 2/1995 | Berk et al. | 504/206 |
| 5,639,711 | 6/1997 | Kassebaum et al. | 504/206 |
| 5,683,958 | 11/1997 | Berger et al. | 252/357 X |

*Primary Examiner*—Richard D. Lovering
*Attorney, Agent, or Firm*—Connolly & Hutz

[57] ABSTRACT

The invention pertains to new composition and a method for increasing the solubility of various agricultural compounds in water at a low pH. The compounds included in this patent are typically not soluble at pH ranges less than 7 to produce commercially viable liquid concentrates. This method requires the use of tallowamine ethoxylates and phosphate esters to lower the pH of various compounds and also keep them soluble in water.

26 Claims, No Drawings

AGRICULTURAL FORMULATION

BACKGROUND OF THE INVENTION

Many agricultural formulations contain water soluble salts. These salts, often alkylamine salts, are generally not as active as their acid equivalents. For example, 2,4-Dichlorophenoxyacetic acid (2,4-D acid) is known to be more herbicidally active than the dimethylamine salt of 2, 4-D. However, the 2, 4-D acid is not soluble in water. Solvents used to formulate, 2,4-D acid are known to be phytotoxic to plants and enhance herbicide volatility and subsequent drift to non-target areas. In another example, boron is known to be available to plants only in the boric acid form. However, boric acid is only soluble at relatively low concentrations in water, while the monoethanolamine salt of boric acid is known to be much more soluble.

U.S. Pat. No. 4,332,609 issued to Ott, which is incorporated by reference in its entirety, discusses the means of producing just such a water soluble concentrate of boric acid and monothanolamine. The disadvantage is that the plants must convert this boric acid monoethanolamine complex to boric acid in order to use it. Furthermore, boron is often applied in conjunction with a variety of agricultural pesticides which are subject to degradation at high pH ranges. The boric acid monothanolamine salt produces high pH solutions and therefore is detrimental to many pesticides.

Fattyamine ethoxylates have been known to be used in agricultural formulations in the past. Specifically, tallowamine ethoxylate surfactant is known to enhance glyphosate activity and translocation.

Phosphate esters of alkylphenolethoxylate and alcohol ethoxylates have been used in agriculture traditionally as buffering agents and compatibility agents. U.S. Pat. No. 4,770,694 assigned to Kao Corp., which is incorporated by reference in its entirety, describes the use of phosphate esters to suspend a water insoluble biocide. However, Kao does not discuss the pH as a relevant factor in solubility, and further does not address water soluble compounds.

U.S. Pat. No. 4,440,562 assigned to Monsanto Company, which is incorporated by reference in its entirety, describes the use of phosphate esters to couple the isopropylamine salt of glyphosate into the water insoluble 2-haloacetanilide herbicide. Again, pH is not a relevant factor and this patent does not address the use of other pesticides than glyphosate.

U.S. Pat. No. 5,389,598 assigned to Monsanto Company, which is incorporated by reference in its entirety, describes a storage stable aqueous composition containing
(a) water-soluble pesticide or plant growth modifying agent,
(b) an alkylamine surfactant,
(c) a $C_6$–$C_{22}$ saturated or unsaturated alkyl monocarboxylic or dicarboxylic acid
(d) and water.

The third ingredient (c) $C_6$–$C_{22}$ saturated or unsaturated alkyl monocarboxylic or dicarboxylic acid is essential and must be present in a ratio alkoxylated alkylamine surfactant to $C_6$–$C_{22}$ saturated alkyl mono or dicarboxylic acid from at least about 2:1. Our invention works with none, essentially none or even a low ratio less than 2:1 such as 1:1 or less of amine to mono-or dicarboxlic acid. Preferably, there is essentially none or even no $C_6$–$C_{22}$ saturated alkyl mono or dicarboxylic acid present. Furthermore, this patent requires the use of acetylenic diol surfactants which are not required by this invention. In fact, this invention works without any acetylenic diol surfactants being present or essentially no acetylenic diol surfactants being present.

SUMMARY OF THE INVENTION

The present invention is a homogenous agricultural liquid composition containing at least an acidic ester surfactant, and an amine containing surfactant, preferably a fatty amine ethoxylate surfactant, at least one other agricultural chemical. The agricultural chemical referred to herein, can used in agricultural or non-applications. The agricultural applications include, but are not limited to pesticide, fertilizer, or plant growth regulators. The non-agricultural applications include, but are not limited to forestry, aquatics, right of way (such as the areas along roads or medians), turf (such as lawns, golf courses etc.) ornamental (such as plants for their beauty) municipal (parks, school, open land, etc).

Optionally, other surfactants or formulation aids can be added. The formulation can have a pH of less than about 7. It is also possible to add a buffering agent to further decrease the pH of the composition. Preferably, the acidic ester surfactant is a phosphate ester and the fatty amine is a tallowamine ethoxylate. The composition allows water soluble salts of agricultural chemicals to remain stable and soluble at lower than normal pH ranges.

DETAILED DESCRIPTION OF THE PREFERRED EMBODIMENT

It has been surprisingly discovered that a wide range of water soluble compounds can be stabilized at lower than normal pH ranges using a combination of acidic ester surfactants and amine containing surfactants such as but not limited to fatty amine ethoxylates. In addition, the composition can contain a phosphate ester surfactant and a tallowamine ethoxylate surfactant.

The acid ester surfactants are of the formula

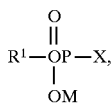

and more preferably of the formula (I) for the diester,

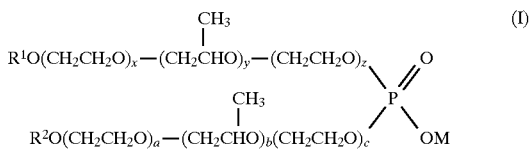

or of the formula (II) for the monoester

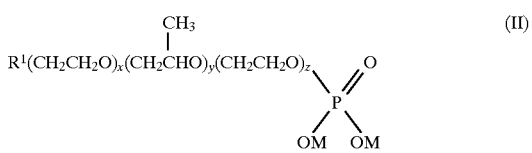

where $R^1$ is —H or and alkyl or akylaryl group, $R^2$ is —H, or an alkyl or alkylaryl group, x, z, a, and c are identical or different and are moles of ethylene oxide and are a number from 0 to 100, and preferably from 1 to 100, y and b are identical or different and represent moles of propylene oxide and are a number from 0 to 100, and the sum of x+y+z+a+b+c should be at least 2, and preferably at least 4.

M is either hydrogen or a counterion such as an alkali metal, an alkaline earth metal, ammonium, alkanolamine or the like.

The preferred acid ester surfactant is a phosphate ester of nonyl-or octylphenol ethoxylates. The acid ester surfactant is more preferably a phosphate ester of linear or branched alcohol ethoxylates. The acid ester surfactant can be present in an amount from about 1 to about 99% of the composition. The acid ester surfactant is preferably present in an amount sufficient to reduce the pH of the product to less than about 7.

The fattyamine alkoxylate can be of the formula

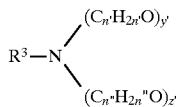

where n' and n" are identical or different and are a number from 2 to 4 and y' and z' are identical or different and are a number from 0 to 100 with the sum of y' and z' is from 2 to about 110 and most preferably from 2 to about 50.

The fattyamine alkoxylate is preferably of the formula

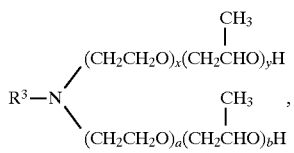

where $R^3$ is a $C_8$–$C_{25}$ alkyl, preferably a fatty alkyl group, x and a are moles of ethylene oxide, and y and b are moles of propylene oxide, x and a are identical or different and are a number from 1 to 100 and y and b are identical or different and are a number from 0 to 100 and preferably from 21 to 100 and most preferably from 2 to about 50.

Additionally, the fatty amine alkoxylate can be a block copolymer derived from the sequential addition of ethylene oxide and propylene oxide to ethylenediamine of the formula

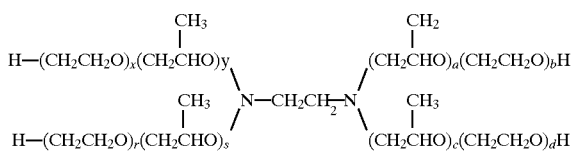

where x, b, r, d are moles of ethylene oxide being identical or different and being da number from 0 to 100, and preferably from 1 to 100, y, a, s, c are moles of propylene oxide being identical or different and being a number from 0 to 100. Preferably the sum of x+b+r+d+y+a+s+c is at least 2, and more preferably the sum is at least 4.

The most preferred fatty amine alkoxylate surfactant is a tallowamine ethoxylate. The fatty amine containing surfactant can be present in an amount from about 1 to about 99%. Preferably, the fatty amine containing surfactant is present in an amount sufficient to enhance the efficacy of the crop protection chemicals.

The agricultural chemical can be a fertilizer containing boron, zinc, copper, iron, blends of nitrogen phosphorous and potash or mixtures thereof. The agricultural chemical can be a crop protecting chemical such as but not limited to a herbicide. The herbicide can be, but not limited to, dimethylamine (DMA) salt of 2,4-dichlorophenoxyacetic acid, DMA salt of dicamba, sodium salt of dicamba, iso- propylamine (IPA) salt of glyphosate, IPA salt of 2,4-dichlorophenoxyacetic acid, sodium salt of acifluorfen, sodium-salt of bentazon, sodium salt of imazethapyr, ammonium salt of imazaquin, IPA salt of imazapyr, sodium salt of asulam or mixtures thereof. The agricultural chemical can be present in an amount from about 1 to about 99%.

The composition can contain micronutrients such as boron. In example I, Ott's patented composition of a monoethanolamine salt of boric acid is further unexpectedly improved by using a blend of phosphate ester and an amine surfactant such as tallowamine ethoxylate.

The agricultural formulation can also contain additional surfactants. The preferred additional surfactants include, but are not limited to:

a) sorbitan fatty acid ester,
b) polyethoxylated derivative of a sorbitan fatty acid ester,
c) fatty alkanolamides of the formula

wherein R is an alkyl group having about 6 to about 25 carbon atoms; R' and R" independently of one another are selected from the group consisting of hydrogen,

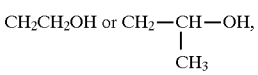

d) peg esters of the formula

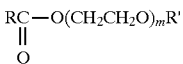

wherein R is a fatty alkyl having from about 2 to about 25 carbon atoms, R' is a fatty alkyl having from about 2 to about 25 carbon atoms or H and m is a number from 1 to about 100, e) silicone surfactants of the formula

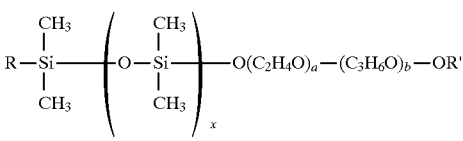

or

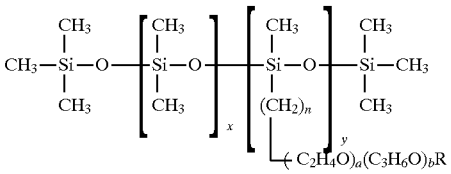

wherein R and R' independently from one another are hydrogen, alkyl having from 1 to about 20 carbon atoms, preferably 1 to 4 carbon atoms or an alkyl ester group having 1 to 20 carbon atoms, preferably 1 to 4 carbon atoms, x is a number from about 1 to about 100, preferably from about 1 to about 5, a is a number from about 3 to about 25, b is a number from about 0 to about 25, n is a number from about 2 to about 4 and f) ethoxylated fatty acids

wherein R is an alkyl group having from about 6 to about 25 carbon atoms, n is a number from 1 to about 100,
g) alkyl ethoxylates

wherein R is an alkyl group having from about 1 to about 50 carbon atoms and x is a number from 1 to about 100,
h) alkylphenol ethoxylates

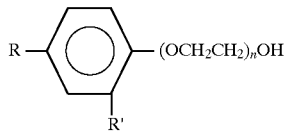

wherein R is H or an alkyl having from about 1 to about 20 carbons, R' is H or an alkyl having from about 1 to about 20 carbons and n is a number from 1 to about 100,
i) polypropylene glycols

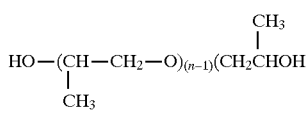

wherein n is a number from 1 to about 100,
j) tristyrylphenol alkoxylates,
k) amine ethoxylates

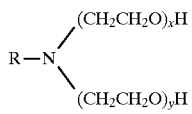

wherein x and y independently of one another are a number from about 1 to about 100 and R is an alkyl having from 1 to about 25 carbon atoms,
l) N-Acyl Sarcosines and Sodium N-Acyl Sarcosinates,
m) alkylaryl polyethoxy phosphate ester,
n) alkylaryl polyethoxy carboxylate ester,
o) tristyrylphenol alkoxylate phosphate esters,
p) tristyrylphenol alkoxylate carboxylate esters,
q) Phosphate esters of block copolymers of ethylene and propylene oxide or
r) alkylpolyglucosides.

Additionally, buffering agents can be added to the composition to further reduce the pH. The buffering agents include, but are not limited to,
a) alkylaryl polyethoxy phosphate ester,
b) $C_1$–$C_6$ carboxylic acids,
c) $C_1$–$C_6$ dicarboxylic acids,
d) phosphoric acid,
e) citric acid,
f) glutaric acid,
g) gluconic acid,
h) lactic acid,
i) glycolic acid,
j) acrylic acid,
k) carboxylated alcohol ethoxylate, preferably of the formula

R is a carboxylic acid having from 1 to about 25 carbon atoms and x is from 1 to about 20 moles ethylene oxide,
l) ethoxylated alkylaryl phosphate esters;
m) ethoxylated alkylphenol carboxylate esters;
n) tristyrylphenol alkoxylate phosphate esters;
o) tristyrylphenol alkoxylate carboxylate esters;
p) fatty acids and blends thereof and
q) phosphate esters of block copolymers of ethylene and propylene oxide.

The formulation can optionally contain water insoluble agricultural chemicals such as but not limited to pesticides. The pesticides can be, but are not limited to ester of dichlorophenoxyacetic acid, trifluralin, pendimethalin, propanil, atrazine, benefin, chloroimuron, linuron, alachlor, metalochlor or mixtures thereof.

Furthermore the agricultural formulation can have a surface tension of less than 60 dynes as measured by the Du Nuoy Surface Tensiometer at a concentration of 1–10%.

The formulation is made by mixing all the ingredients together. Other optional ingredients include but are not limited to dyes, thickeners, anti-corrosion agent, anti-caking agents, stabilizers, gel inhibitors, anti-freezes, anti-foam agents, mixtures thereof and the like.

The following examples are listed to help illustrate the advantage of the new agricultural formulation.

EXAMPLE 1

| Ingredients | % in formula |
|---|---|
| Monoethanolamine salt of boric acid | 80.0 |
| Tallowamine ethoxylate surfactant | 10.0 |
| Phosphate ester surfactant | 10.0 |

The improvement of this formula is in the resulting pH of the composition. The monoethanolamine salt of boric acid has a pH of 9.0 on its own. The composition of Example 1 has a pH of 6.65. It is generally acknowledged in most agricultural applications that plants can only use boron in it's acidic form. However, the solubility of boric acid alone is very low at pH ranges less than 8.0. Therefore, as evidenced in the patent issued to Ott containing monoethanolamine salt composition, most agricultural boron formulations use high pH solutions to increase boron solubility, and rely on environmental conversion of the boron to lower pH form which can then be used by plants.

The patented composition can contain pesticides such as the dimethylamine salt of 2,4-Dichlorophenoxyacetic acid (2,4-D Amine). In Example 2, a dimethylamine salt of 2,4-D is formulated which with phosphate ester surfactants, tallowamine ethoxylate surfactant, and other wetting agents. The resulting composition has a pH of about 4.5, as opposed to conventional dimethylamine salt of 2,4-D formulations which have a pH of about 8.5. Furthermore, the formulation is significantly more compatible with liquid fertilizer solutions. In mixes containing only urea-ammonia nitrate fertilizer, the traditional 2,4-D Amine product formed crystals. The formulation in Example 2 produced a nice clear solution.

EXAMPLE 2

| Ingredients | % in formula |
| --- | --- |
| Dimethylamine salt of 2,4-D | 69.80 |
| Tallowamine ethoxylate surfactant | 6.00 |
| Phosphate ester surfactant | 14.00 |
| Citric acid | 0.70 |
| Alcohol ethoxylate surfactant | 2.00 |
| Water | 7.50 |

The stability of the composition in Example 2 is excellent, over more than 2 months in accelerated storage tests, and therefore is expected to be stable at normal temperatures for at least 2 years. Furthermore, efficacy trials showed enhanced herbicide activity with the formulation of Example 2 when compared with commercial 2,4-D Amine products.

In Example 3 the compatibility of two water soluble herbicides is enhanced using phosphate ester surfactants and tallowamine ethoxylate surfacts. Plateau herbicide is a water-based formulation, containing the active ingredient, imazameth, and manufactured by American Cyanamid. Garlan 3A herbicide is a water based formulation containing the triethylamine salt of triclopyr, and manufactured by Dow Elanco. These two products cannot be mixed at normal use rates without dilution by water. A typical tank mix of these two herbicides would contain 4 ounces of Plateau and 32 ounces of Garlon 3A. A direct mixture of these herbicides salt out quickly. The addition of nearly 50 ounces of water is required to keep these herbicides solubilized for extended periods of time. The addition of as little as 21 ounces of an adjuvant containing tallowamine ethoxylates and phosphate ester surfactants maintains the solubility of the herbicide mixture.

In Example 4, a dimethylamine salt of 2,4-D is formulate with phosphate ester block copolymer surfactants, a block copolymer derived from the sequential addition of ethylene oxide and propylene oxide to ethylenediamine, and other wetting agents. The resulting composition has a pH of about 5.0, as opposed to conventional dimethylamine salt of 2,4-D formulations which have a pH of about 8.5.

EXAMPLE 4

| Ingredients | % in formula |
| --- | --- |
| Dimethylamine salt of 2,4-D | 69.80 |
| EO/PO Block Copolymer of Ethylenediamine | 5.00 |
| Phosphate ester EO/PO Block Copolymer | 5.00 |
| Alcohol ethoxylate surfactant | 5.00 |
| Water | 15.20 |

The inventive composition can be used in a method of controlling vegetation by adding the inventive composition to foliage of plants. Further, the inventive composition can be used in a method of promoting plant growth and/or eliminating the damage caused by insects by adding the inventive composition to foliage of plants.

While there is shown and described certain specific structures embodying the invention, it will be manifest to those skilled in the art that various modifications and rearrangements of the parts may be made without departing from the spirit and scope of the underlying inventive concept and that the same is not limited to the particular forms herein shown and described.

We claim:

1. A composition which consists essentially of:
   (a) at least one acid ester surfactant of the formula (I) or (II)

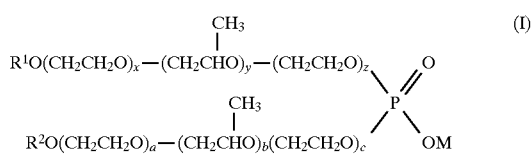

or

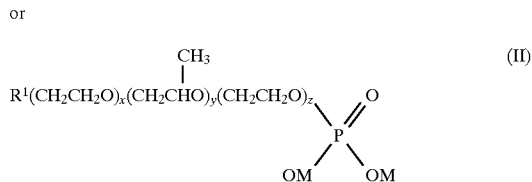

where $R^1$ is H or and alkyl or alkylaryl group
   $R^2$ is H, alkyl or alkylaryl group,
   M is hydrogen, sodium or ammonium counterion,
   x, y, z, a, b and c are identical or different and are a number from 0 to 100, with the proviso that x+y+z+a+b+c is at least 2,
   (b) at least one amine containing surfactant and
   (c) at least one water soluble agricultural chemical.

2. The composition as claimed in claim 1, which comprises (a) at least one acid ester surfactant of the formula (I) or (II)

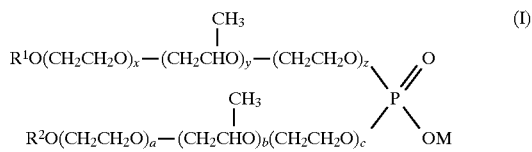

or

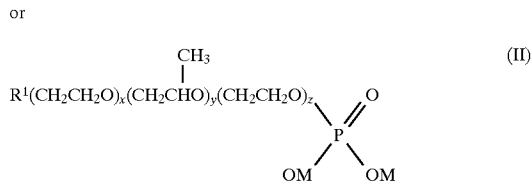

where R' is —H or and alkyl or akylaryl group,
   $R^2$ is —H, alkyl or alkylaryl group,
   M is hydrogen, sodium or ammonium counterion,
   x, y, z, a, b and c are identical or different and are a number from 0 to 100, with the proviso that x+y+z+a+b+c is at least 2,
   (b) a fattyamine alkoxylate having the formula

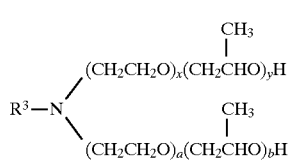

where $R^3$ is a fatty alkyl group,
   x, y, a and b are identical or different and are a number from 0 to 100, with the proviso that x+y+a+b is at least 2, and
   (c) a water soluble agricultural chemical.

3. The composition as claimed in claim 1, wherein the composition has a surface tension of less than 60 dynes as measured by the Du Nuoy Surface Tensiometer at a concentration of 1–10%.

4. The composition as claimed in claim 1, wherein the acid ester surfactant is a phosphate ester of nonyl-or octylphenol ethoxylates.

5. The composition as claimed in claim 4, wherein the amine containing surfactant is a tallowamine ethoxylate and said composition has a final pH of less than about 7.

6. The composition as claimed in claim 5, wherein the agricultural chemical is a herbicide contains at least one of chemicals selected from the group consisting of dimethylamine (DMA) salt of 2,4-dichlorophenoxyacetic acid, DMA salt of dicamba, sodium salt of dicamba, isopropylamine (IPA) salt of glyphosate, IPA salt of 2,4-dichlorophenoxyacetic acid, sodium salt of acifluorfen, sodium salt of bentazon, sodium salt of imazethapyr, ammonium salt of imazaquin, IPA salt of imazapyr and sodium salt of asulam.

7. The composition as claimed in claim 1, wherein the acid ester surfactant is a phosphate ester of linear or branched alcohol ethoxylates.

8. The composition as claimed in claim 1, wherein the amine containing surfactant is a tallowamine ethoxylate.

9. The composition as claimed in claim 1, wherein the agricultural chemical is a fertilizer.

10. The composition as claimed in claim 9, wherein the fertilizer contains at least one of the following ingredients selected from the group consisting of boron, zinc, copper, iron and blends of nitrogen, phosphorous and potash.

11. The composition as claimed in claim 1, wherein the agricultural chemical is a herbicide.

12. The composition as claimed in claim 11, wherein the herbicide contains at least one of chemical selected from the group consisting of dimethylamine (DMA) salt of 2,4-dichlorophenoxyacetic acid, DMA salt of dicamba, sodium salt of dicamba, isopropylamine (IPA) salt of glyphosate, IPA salt of 2,4-dichlorophenoxyacetic acid, sodium salt of acifluorfen, sodium salt of bentazon, sodium salt of imazethapyr, ammonium salt of imazaquin, IPA salt of imazapyr and sodium salt of asulam.

13. The composition as claimed in claim 1, which further contains additional surfactants.

14. The composition as claimed in claim 1, which further comprises a water insoluble crop protection chemical.

15. The composition as claimed in claim 14, wherein said water insoluble crop protection chemical is at least one chemical selected from the group consisting of ester of dichlorophenoxyacetic acid, trifluralin, pendimethalin, propanil, atrazine, benefin, chloroimuron, linuron, alachlor and metalochlor.

16. The composition as claimed in claim 1, wherein said composition has a final pH of less than about 7.

17. The composition as claimed in claim 1, wherein said composition has a final pH of between about 4 to about 6.

18. A method to control vegetation which comprises applying the composition as claimed in claim 1 to foliage of plants.

19. A method of promoting plant growth and/or eliminating the damage to the plant which comprises adding the composition as claimed in claim 1 to foliage of plants.

20. A composition consisting essentially of:
(a) at least one acid ester surfactant of the formula (I) or (II)

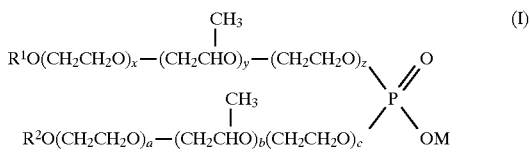

or

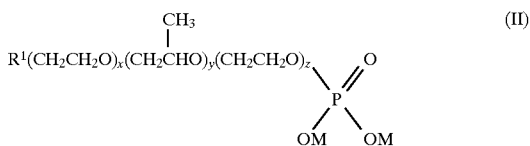

where
$R^1$ is —H or an alkyl or alkylaryl group,
$R^2$ is —H or an alkyl or alkyl aryl group,
M is hydrogen, sodium or ammonium counterion,
x, y, z, a, b and c are identical or different and are a number from 0 to 100, with the proviso that the sum of x+y+z+a+b+c is at least 2,
(b) a block copolymer derived from the sequential addition of ethylene oxide and optionally propylene oxide to form an ethylenediamine of the formula

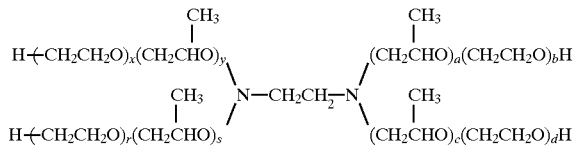

where x, y, a, b, c, d, r, and s are identical or different and are a number from 0 to 100, with the proviso that sum of x+y+a+b+c+d+r+s must be at least 2 and
(c) a water soluble agricultural chemical.

21. The composition as claimed in claim 20, wherein said composition has a final pH of less than about 7.

22. The composition as claimed in claim 20, wherein said composition has a final pH of about 4 to about 6.

23. A composition which comprises
(a) at least one acid surfactant of the formula (I) or (II,)

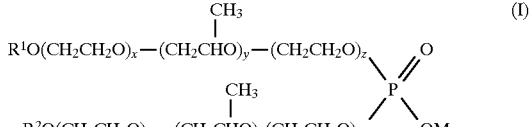

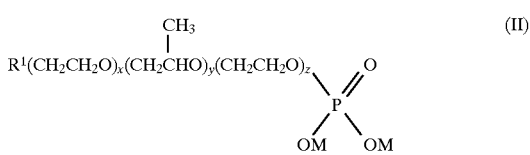

where R' is H, alkyl or alkylaryl group,
$R^2$ is H, alkyl or alkylaryl group,
M is a counter ion,
x, y, z, a, b and c are identical or different and are a number from 0 to 100, with the proviso that x+y+z+a+b+c is at least 2,
(b) at least one amine containing surfactant and
(c) at least one water soluble agricultural chemical.

24. The composition as claimed in claim 23, wherein M is alkali metal, an alkaline earth metal, ammonium or an alkanolamine.

25. A composition which comprises (a) at least one acid surfactant of the formula (I) or (II,)

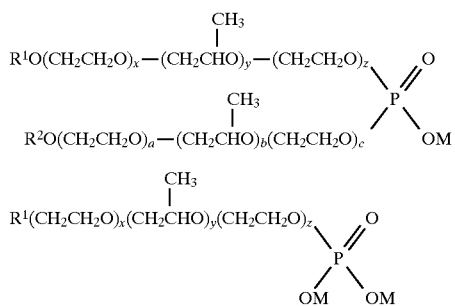

where R¹ is H or alkyl,

R² is H or alkyl,

M is H or a counter ion, x, y, z, a, b and c are identical or different and are a number from 0 to 100, with the proviso that x+y+z+a+b+c is at least 2, (b) at least one amine containing surfactant and (c) at least one water soluble agricultural chemical.

26. The composition as claimed in claim 25, wherein M is alkali metal, an alkaline earth metal, ammonium or an alkanolamine.

* * * * *